(12) United States Patent
Hammann et al.

(10) Patent No.: US 7,705,292 B2
(45) Date of Patent: Apr. 27, 2010

(54) METHOD AND APPARATUS FOR DETECTING A CONDITION OF AN OPTICAL ELEMENT

(75) Inventors: Gerhard Hammann, Korntal-Muechingen (DE); Dieter Hallasch, Ditzingen (DE); Juergen Hohenadel, Schwieberdingen (DE)

(73) Assignee: TRUMPF Werkzeugmaschinen GmbH + Co. KG, Ditzingen (DE)

( * ) Notice: Subject to any disclaimer, the term of this patent is extended or adjusted under 35 U.S.C. 154(b) by 0 days.

(21) Appl. No.: 12/139,381

(22) Filed: Jun. 13, 2008

(65) Prior Publication Data

US 2009/0007675 A1 Jan. 8, 2009

Related U.S. Application Data

(63) Continuation-in-part of application No. PCT/EP2005/013534, filed on Dec. 15, 2005.

(51) Int. Cl.
*G01H 5/00* (2006.01)

(52) U.S. Cl. .................. 250/238; 250/221; 372/34; 372/29.01; 374/117; 374/119

(58) Field of Classification Search .............. 250/238, 250/221; 372/34, 29.01; 374/117, 119
See application file for complete search history.

(56) References Cited

U.S. PATENT DOCUMENTS 6,118,527 A 9/2000 Jurca 6,370,171 B1 4/2002 Horn et al.
6,517,240 B1 * 2/2003 Herb et al. .................. 374/117

FOREIGN PATENT DOCUMENTS

| DE | 4300378 | 7/1993 |
|---|---|---|
| DE | 9403822 | 8/1995 |
| DE | 19709473 | 9/1998 |
| DE | 10007976 | 9/2001 |
| DE | 10108955 | 10/2002 |
| DE | 20306411 | 8/2003 |
| DE | 20314918 | 3/2005 |
| DE | 102004006565 | 9/2005 |
| EP | 0988916 | 3/2000 |
| EP | 1310782 | 5/2003 |
| EP | 1354664 | 10/2003 |
| EP | 1398612 | 3/2004 |
| EP | 1488882 | 12/2004 |
| EP | 1643281 | 4/2006 |
| JP | 62139347 | 6/1987 |
| JP | 62139374 | 6/1987 |
| WO | WO 98/33059 | 7/1998 |

OTHER PUBLICATIONS

International Search Report and Written Opinion from corresponding PCT Application No. PCT/EP2005/013534, mailed Aug. 23, 2006, 12 pages.

(Continued)

*Primary Examiner*—Seung C Sohn
(74) *Attorney, Agent, or Firm*—Fish & Richardson P.C.

(57) ABSTRACT

A condition or detecting a change in the condition of an optical element of a laser arrangement is detected. An ultrasonic signal is coupled into an optical element such that the ultrasonic signal travels along a path within the optical element, and a transit time or a change in transit time for the ultrasonic signal to travel along the path within the optical element is detected.

26 Claims, 4 Drawing Sheets

OTHER PUBLICATIONS

Transmittal of International Preliminary Report on Patentability from corresponding PCT Application No. PCT/EP2005/013534, mailed Jun. 28, 2008, 7 pages.

Transmittal of Translation of International Preliminary Report on Patentability from corresponding PCT Application No. PCT/EP2005/013534, mailed Jul. 17, 2008, 6 pages (in English).

* cited by examiner

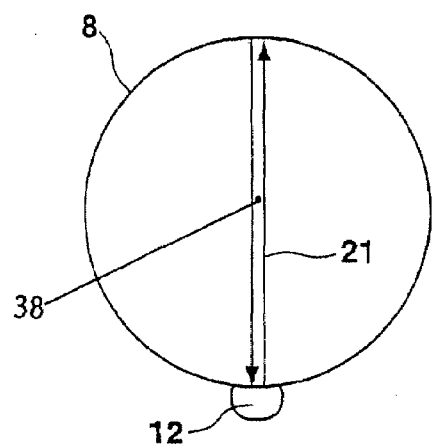
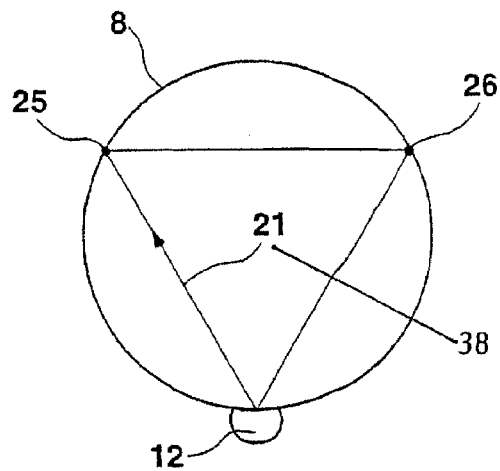
Fig. 3a Fig. 3b
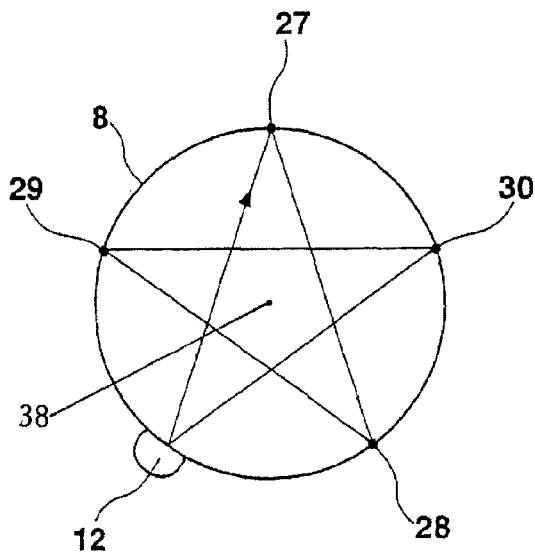
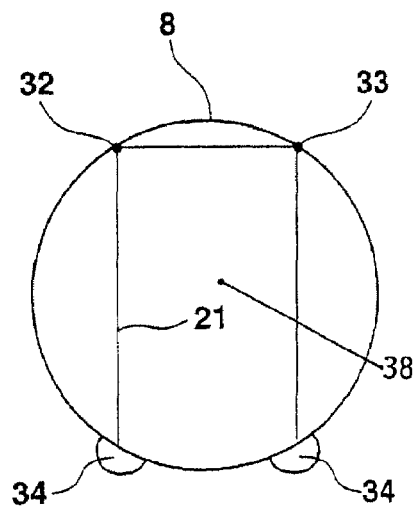
Fig. 3c Fig. 3d

METHOD AND APPARATUS FOR DETECTING A CONDITION OF AN OPTICAL ELEMENT

CROSS-REFERENCE TO RELATED APPLICATIONS

This application is a continuation-in-part of and claims priority under 35 U.S.C. §120 to PCT Application No. PCT/EP2005/013534, filed on Dec. 15, 2005. The contents of this priority application is hereby incorporated by reference in its entirety.

TECHNICAL FIELD

This disclosure relates to techniques for detecting a condition or a change in the condition of an optical element included in a laser arrangement, in which a parameter that varies with a change in the temperature of the optical element is detected.

BACKGROUND

Among other aspects, a laser cutting process depends on the quality and temporal behaviour of a focussed laser beam used in the laser cutting process. Lenses and/or mirrors are used to guide and form the laser beam. Thus, the lenses and/or mirrors influence the resulting cut. Wear on the lenses (or on other optical elements in the beam path) can increase the absorption of the laser beam by the lenses or other optical elements, which results in heating of the lenses or other optical elements. The heating can cause changes in the optical properties of the lenses or other optical elements, such as, for example, a greater focal shift.

Because a change in the temperature of the optical element frequently causes a change in the condition of the optical element, various techniques have been proposed to detect the temperature of an optical element or a parameter describing this. For example, a resistance measurement is disclosed in European Patent No. EP 1 310 782 A1. A change in a physical parameter of an optical element such as, for example, the temperature, due to the absorbed radiation is sensed and used as a source of information of the condition of the optical element. In this method the temperature is determined by measuring an electrical resistance. In German Utility Patent No. 203 14 918 U1, a device for monitoring a protective glass in a system of laser optics for breakage and/or contamination is disclosed. In German Patent Application No. 10 2004 006 565 A1, a change in length of an optical element is measured. A temperature change that is due to a change in the optical properties is determined based on the measured change in length.

In German Patent Application No. 197 094 73 A1, a degree of wear of a lens arrangement is determined during the machining of a workpiece with a laser beam. The workpiece is cut with the laser beam, and a cut-in time required to cut through the workpiece is measured and compared with a predetermined reference cut-in time to generate, for example, a warning signal if both cut-in times deviate from each other by more than a given tolerance value. A trace on the workpiece is generated with the laser beam, and at different times the radiation coming from the workpiece is measured, in order to deduce the wear condition of the lens arrangement by comparing the measured radiation values taken at different times. In International Patent Application Publication No. WO 98/33059, a photodetector detects scattered light generated by contamination.

SUMMARY

In one general aspect, a condition or detecting a change in the condition of an optical element of a laser arrangement is detected. An ultrasonic signal is coupled into an optical element such that the ultrasonic signal travels along a path within the optical element, and a transit time or a change in transit time for the ultrasonic signal to travel along the path within the optical element is detected.

Implementations can include one or more of the following features. Detecting a change in transit time can include detecting a current transit time and comparing the current transit time to a predetermined transit time. The path can be a predetermined path. The path can be specified before coupling the ultrasonic signal into the optical element. A degree of absorption of electromagnetic radiation of the optical element can be determined based on the detected transit time or change in transit time. Determining a degree of absorption of electromagnetic radiation of the optical element can include determining a degree of absorption and comparing the degree of absorption to a base degree of absorption. A temperature or a change in temperature of the optical element can be determined based on the detected transit time. The path can pass through the center of the optical element. The ultrasonic signal can be radially coupled into the optical element. The path can pass through peripheral regions of the optical element without passing through the center of the optical element. The path of the ultrasonic signal can pass through the optical element multiple times. A transit time gradient can be determined.

The optical element can be irradiated with electromagnetic radiation, and detecting a transit time or a change in transit time of the ultrasonic signal to travel along the path within the optical element can include detecting the transit time during the irradiation and for a time period following the ending of the irradiation. The time period can be determined before irradiating the optical element with electromagnetic radiation. The electromagnetic radiation can be laser radiation. The optical element can be irradiated intermittently with electromagnetic radiation. The transit time can be detected in a set time interval. Parameters describing the environment of the optical element can be detected, and the transit times can be analyzed based on the detected parameters. A characteristic diagram can be generated, and a current transit time can be analyzed using the characteristic diagram.

In another general aspect, a laser arrangement includes at least one optical element arranged in the beam path of a laser beam, a detection device for detecting a parameter of the optical element that varies with a change in temperature, an ultrasonic transmitter configured to couple an ultrasonic signal into the optical element, and an ultrasonic receiver included in the detection device.

Implementations can include one or more of the following features. The detection device can include the ultrasonic transmitter and the ultrasonic receiver. At least one reflector can be configured to reflect the ultrasonic signal. At least one coupling element can be arranged between the optical element and one of the ultrasonic transmitter or the ultrasonic receiver. The coupling element can be matched to the optical element. An analysis device can be connected to the detection device.

To determine a condition or a change of an optical element, an ultrasonic signal is coupled into the optical element and the transit time and/or a change in the transit time of the ultrasonic signal along a prespecified or prespecifiable path through the optical element is detected. The optical element can be included in a laser arrangement such as a laser processing machine. The techniques discussed below can be used for any optical element (e.g., mirrors, lenses, decouplers) included in the laser arrangement, and also for optical elements in the laser. The determined transit time, or the change in transit time, can be compared with a reference value (which also can be referred to as a base value). The reference value can be determined in a reference value measurement or the reference value can be predefined. The measurement of the transit time can be carried out with standard components, and the measurement of the transit time can take place without affecting the remaining laser arrangement. Even small temperature changes cause a change in the transit time of the ultrasonic signal, thus, the temperature of the optical element can be measured or determined with a high resolution. A suitable choice of the path through the optical element can ensure that only the actual temperature, or the associated transit time or transit time change caused by a temperature change in the optical element, is detected, and the measurement is not distorted by the temperature for example of a holder of the optical element. The resolution of the transit time measurement should preferably be in the nanosecond region.

In one implementation, a degree of absorption of electromagnetic radiation, or a change in the degree of absorption by the optical element can be determined from the transit time and/or the transit time change. Thus, by determining the transit time or a change in the transit time therefore, conclusions can be drawn as to contamination or wear, for example as a consequence of ageing phenomena, in the optical element. The technique can distinguish between a change in transit time due to a normal temperature change (heating) of the optical element in operation and a change in transit time due to an absorption related temperature increase.

The temperature or a temperature change of the optical element can be deduced from the transit time and/or transit time change. A measure for the wear is provided by both the constant temperature of the optical element and a temporal temperature gradient. Using the transit time measurement, the temperature of the optical element averaged over the path covered by the ultrasonic signal can be determined.

The specified or specifiable path can be chosen in such a way that the path passes through the center or near to the center of the optical element. For example, the specified or specifiable path can be chosen to pass through a midpoint of the optical element. Selecting such a path allows the temperature in the center of the optical element to be determined, or at least the temperature in the center of the optical element is included in the temperature averaged over the path. The temperature can thus be detected in the part of the optical element that is heated the most when a laser beam traverses the optical element. In implementations that include an optical element that has a round shape, the ultrasonic signal can be coupled into the optical element radially.

When the path only passes through peripheral regions of the optical element, such as regions that do not include the center of the optical element, information on wear and contamination in the peripheral regions of the optical element can be determined.

The ultrasonic signal can be passed through the optical element multiple times by reflection. The use of reflections offers the possibility of using only one transducer (for sending and receiving the ultrasonic signal). Furthermore, the transit time and therefore the resolution of the system can be increased using single or multiple reflections. By reflecting the ultrasonic signal within the optical element, the ultrasonic signal can pass through specific regions of the optical element. By sending the ultrasonic signal through different regions of the optical element, the different regions of the optical element can be included to detect a change in transit time (and therefore a temperature measurement) due, for example, to local heating of the optical element. The change in transit time due to local heating might not be detectable with only one straight path through the optical element that does not pass through the area of local heating. The ultrasonic signal can be passed through the optical element, for example, in a star-shaped, triangular or rectangular path.

In some implementations, a transit time gradient is determined. From the transit time gradient, a temperature gradient can be determined. When the temperature of the optical element changes, the optical element reacts with a certain delay, which is determined by a time constant. The time constant of the optical element can be in the range of 5-10 seconds. If an absolute temperature is to be detected, the operator waits until the temperature of the optical element is stable. If a temperature gradient is being determined, the measurement can be performed in shorter time intervals. Differences in the absorption of the optical elements can be detected by different gradients of the transit time change. This can supply information on the ageing or the wear of an optical element respectively.

In some implementations, the optical element can be irradiated by an electromagnetic radiation, such as laser radiation emitted from a laser, and the transit time and/or transit time change can be detected during the irradiation of the optical element by the electromagnetic radiation and for a specified or specifiable time period after the end of the irradiation.

By this technique, temperature induced transit time changes of an optical element can be determined. During the period when the laser is switched "on," such that the laser emits laser radiation irradiates the optical element, the optical element warms up. The optical element cools down again after the laser is switched off.

If the optical element is irradiated with electromagnetic radiation several times, for example the optical element can be irradiated with electromagnetic radiation over time intervals, perturbations in the measurement of the transit time or the transit time change can be detected. The transit time or transit time change can be detected over prespecified or prespecifiable time intervals. By specifying the time intervals, the resolution of the temperature measurement can be adjusted.

The inspection of the condition of an optical element can take place during operation, such as during a cutting process. This type of inspection can be considered to be quasi "online." Inspection during operation allows rapid reactions to be made to changes in the condition. Alternatively or additionally, at the beginning of a new cutting process, the condition of the optical element can be inspected. For example, if a laser system with low laser power is being used and a temperature change is not detectable at this low laser power, the laser can be operated between two cutting processes at a higher power, so that transit time changes and the condition of the optical element can be determined.

In some implementations, parameters of the environment of the optical element are detected and/or specified and taken into account in the analysis of the transit times and/or transit time changes. The heating of the optical element is dependent on several parameters of the environment of the optical element. Parameters of the environment include, for example, the laser power, the duration of the radiation and the cooling of the optical component (for example using a cutting gas). For determining absorption of the optical element, these parameters can be determined and taken into account. Current changes in the temperature of the optical element can also be detected. This information can be used if necessary for controlling the power of the laser.

A characteristic diagram can be generated based on the parameters describing the environment, and a current transit time or transit time change can be analysed using the characteristic diagram. The characteristic diagram relates the transit time of the ultrasonic signal, or a change in transit time of the ultrasonic signal, to a temperature. Thus, if the transit time or change in transit time is known, the characteristic diagram can be used to determine a temperature corresponding to the transit time or change in transit time. The characteristic diagram is associated with a particular optical element, and the characteristic diagram can be determined by measuring transit times, or transit time changes and corresponding temperatures for the particular optical element.

In another implementation a laser arrangement, such as a laser processing machine includes at least one optical element. The optical element is arranged in the beam path of a laser beam and includes a detection device for detecting a parameter that varies with a change in temperature of the optical element. An ultrasonic transmitter couples an ultrasonic signal into the optical element, and the detection device includes an ultrasonic receiver. The current condition of the optical element can be detected and changes in the condition of the optical element, for example warming due to absorption caused by contamination or wear of the optical element, can be detected. The optical element can be, for example a mirror, a lens, or a decoupler. The ultrasonic transmitter and the ultrasonic receiver can be arranged at different places in the area of the optical element, and the ultrasonic receiver is placed at the end of the path traversed by the ultrasonic signal. For example, the path of the ultrasonic signal can correspond to a diameter of the optical element. The ultrasonic receiver and ultrasonic transmitter are arranged to face each other. The detection device can be constructed as an ultrasonic receiver.

In some implementations, the detection device includes the ultrasonic transmitter and the ultrasonic receiver. This implementation can help reduce costs of the system because the system includes only one ultrasonic transducer that both sends and receives ultrasonic signals. In this implementation, the ultrasonic signal must undergo one or more reflections such that that the ultrasonic signal returns to the transducer again. When at least one reflector is provided for reflecting the ultrasonic signal, the path traversed by the ultrasonic signal can be artificially lengthened. This measure allows the resolution to be increased. For example, a 1-degree Celsius change in temperature of an optical element can cause the transit time of the ultrasonic signal along a path to increase by 1 nanosecond (ns). A measurement device having an accuracy of 2 nanoseconds (ns) would not detect the 1 ns increase. However, increasing the path length results in a corresponding increase in the time for the ultrasonic signal to travel along the path. Thus, the measurement device can detect the larger increase in the transit time of the ultrasonic signal. Additionally, the effects of a smaller temperature change can be measured.

In order to prevent reflections between the ultrasonic transducer, in particular the ultrasonic receiver, and the optical element, at least one coupling element can be arranged between an ultrasonic transmitter or ultrasonic receiver and the optical element. An ultrasonic signal in the 10 MHz range is not transmitted in air or in a gas, but such an ultrasonic signal is reflected by the optical element. By using the coupling element between the ultrasonic transmitter and ultrasonic receiver on one side and optical element on the other, the ultrasonic signal is coupled into the optical element and decoupled out of the optical element. The coupling element can be clamped on to the edge of the optical element by means of the transducer in such a way that a sonic cone of the ultrasonic signal impinges on the opposite edge of the optical element through the centre of the optical element, and the ultrasonic signal is reflected from the opposite edge of the optical element back to the transducer. In order to improve coupling of the ultrasonic signal into the optical element, the coupling element can be matched to the optical element. For example, the coupling element can be a deformable coupling pad. The deformable coupling pad can be made of a plastic, such as polyurethane, that has sufficient temperature stability.

In some implementations, an analysis device is connected to the detection device. The analysis device analyzes transit times and transit time changes. The analysis device can interact with a signalling device that outputs a signal to indicate that an optical element has an increased absorption. Alternatively or additionally, the analysis device can be connected to a control system for the laser arrangement, such that the information on the condition or changes in the condition of the optical element during the operation of the laser arrangement can be taken into account and used to adjust parameters of the laser arrangement, such as the power of a laser included in the laser arrangement.

Further features and advantages of the techniques discussed above ensue from the following description of examples, from the figures, and from the claims. The individual features can be put into effect in a variant of the techniques discussed either individually, or in a plurality of any kind of combination.

DESCRIPTION OF THE DRAWINGS

FIGS. 3A-3D are schematic illustrations example paths of an ultrasonic signal.

DETAILED DESCRIPTION

Figure 1:
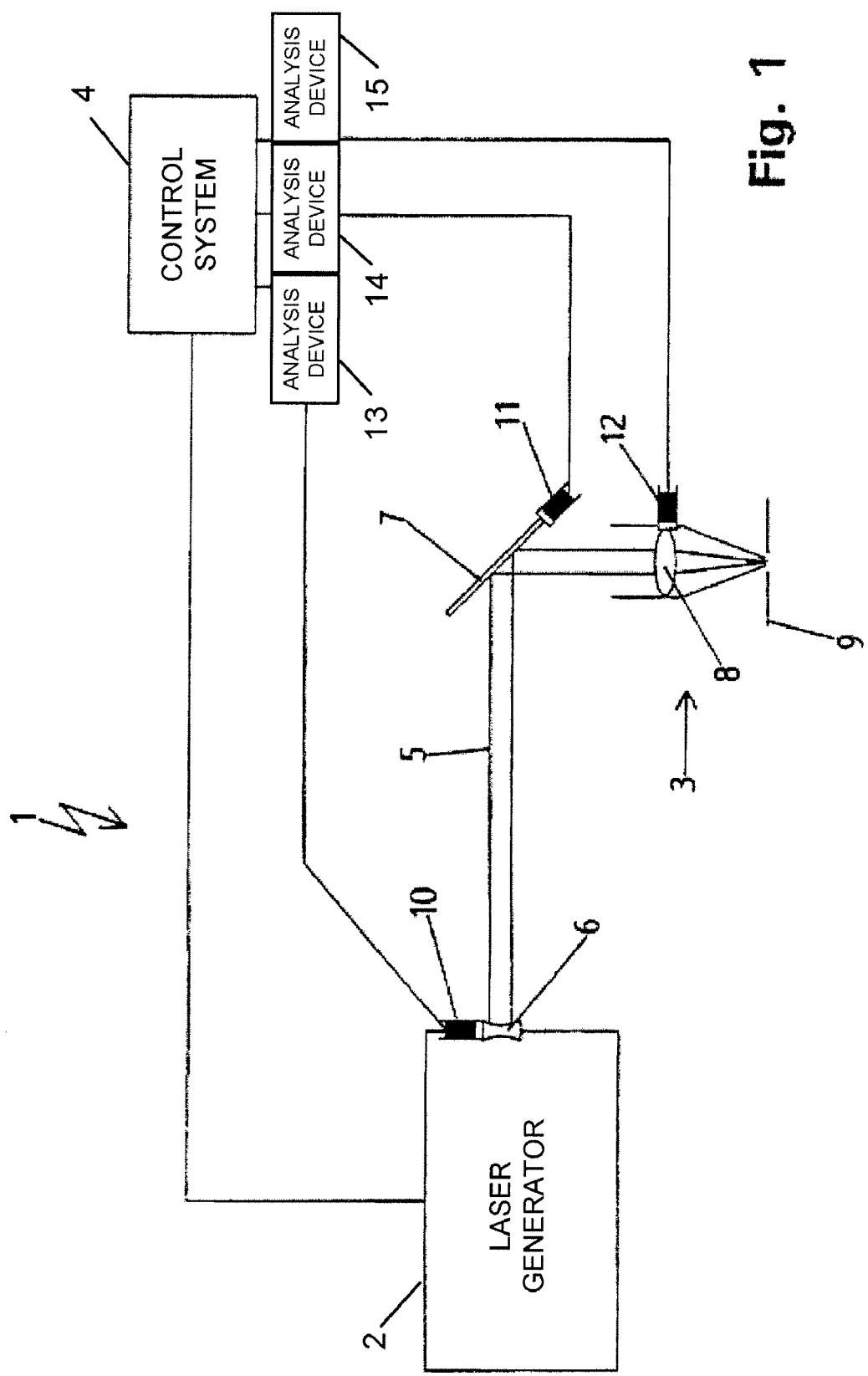
FIG. 1 is a schematic illustration of an example laser arrangement.

Referring to FIG. 1, a laser arrangement 1, such as a laser processing or laser cutting machine, includes a laser generator 2, a processing head 3, and a control system 4. A laser beam 5 is generated in the laser generator 2. Interspersed in the beam path of the laser beam 5 are optical elements such as a decoupling lens 6 of the laser generator 2, a deflecting mirror 7, and a focusing lens 8. In the example shown in FIG. 1, the focusing lens 8 is included in the processing head 3. The focusing lens 8 focuses the laser beam 5 onto a workpiece 9, which is processed by the laser arrangement 1.

A temperature of the decoupling lens 6, the deflecting mirror 7, and the focusing lens 8 are monitored. Detection devices 10, 11, 12 in the form of ultrasonic transducers are used to respectively monitor the temperature of the decoupling lens 6, the deflecting mirror 7, and the focusing lens 8. Each of the detection devices 10, 11, 12 includes an ultrasonic transmitter and an ultrasonic receiver. The detection devices 10, 11, 12 are each connected to analysis devices 13, 14, 15, which are connected to the control system 4. The ultrasound transit time or the change in transit time of an ultrasonic signal through a path of the optical element is detected and analysed by one or more of the analysis devices 13, 14, 15. The change in transit time of the ultrasonic signal can be determined by detecting the transit time of the ultrasonic signal and comparing the transit time to a reference, or base, transit time. For example, the base transit time can be a transit time detected when the optical element is cool or when the optical element has not been contaminated. From this information, data on the degree of electromagnetic absorption by the optical elements and on the temperature or temperature gradients of the optical elements can be derived, where the electromagnetic absorption is the degree that the optical element absorbs the light of the laser beam 5. The degree of absorption can represent the amount of radiation absorbed by the optical element as radiation passes through the optical element. Optical elements that absorb higher amounts of radiation heat up more rapidly than optical elements that have a lower degree of absorption. Thus, optical elements that have a higher degree of absorption can deteriorate (for example, by burning) more quickly.

The analysis devices 13, 14, 15 analyze transit times of an ultrasonic signal travelling through a path in the optical elements (such as the lens 6, the deflecting mirror 7, and the focusing lens 8) and transit time changes of the ultrasonic signal travelling through the path in the optical elements. The analysis devices 13, 14, 15 can interact with a signalling device that outputs a signal to indicate that an optical element has an increased absorption to the electromagnetic radiation that impinges upon the optical element (due to the laser beam 5). Alternatively or additionally, the analysis devices 13, 14, 15 can be connected to the control system 4 for the laser arrangement 1, such that the information on the condition or changes in the condition of the optical element during the operation of the laser arrangement 1 can be taken into account and used to adjust parameters of the laser arrangement 1. Parameters of the laser arrangement 1 include, for example, the power of the laser beam 5.

In some implementations, parameters of the environment of the optical elements are detected and/or specified and taken into account in the analysis of the transit times and/or transit time changes. For example, the heating of the optical element is dependent on several parameters of the environment of the optical element. Parameters of the environment include, for example, the power of the laser beam 5, the duration of the radiation from the laser beam 5, and the cooling of the optical component during processing (for example cooling by using a cutting gas). Current changes in the temperature of the optical element can also be detected. This information can be used if necessary for controlling the power of the laser.

A characteristic diagram can be generated based on the parameters describing the environment, and a current transit time or transit time change can be analysed using the characteristic diagram. The characteristic diagram relates the transit time of the ultrasonic signal, or a change in transit time of the ultrasonic signal, to a temperature. Thus, if the transit time or change in transit time is known, the characteristic diagram can be used to determine a temperature corresponding to the transit time or change in transit time. The characteristic diagram is associated with a particular optical element, and the characteristic diagram can be determined by measuring transit times, or transit times, and corresponding temperatures for the particular optical element.

Figure 2:
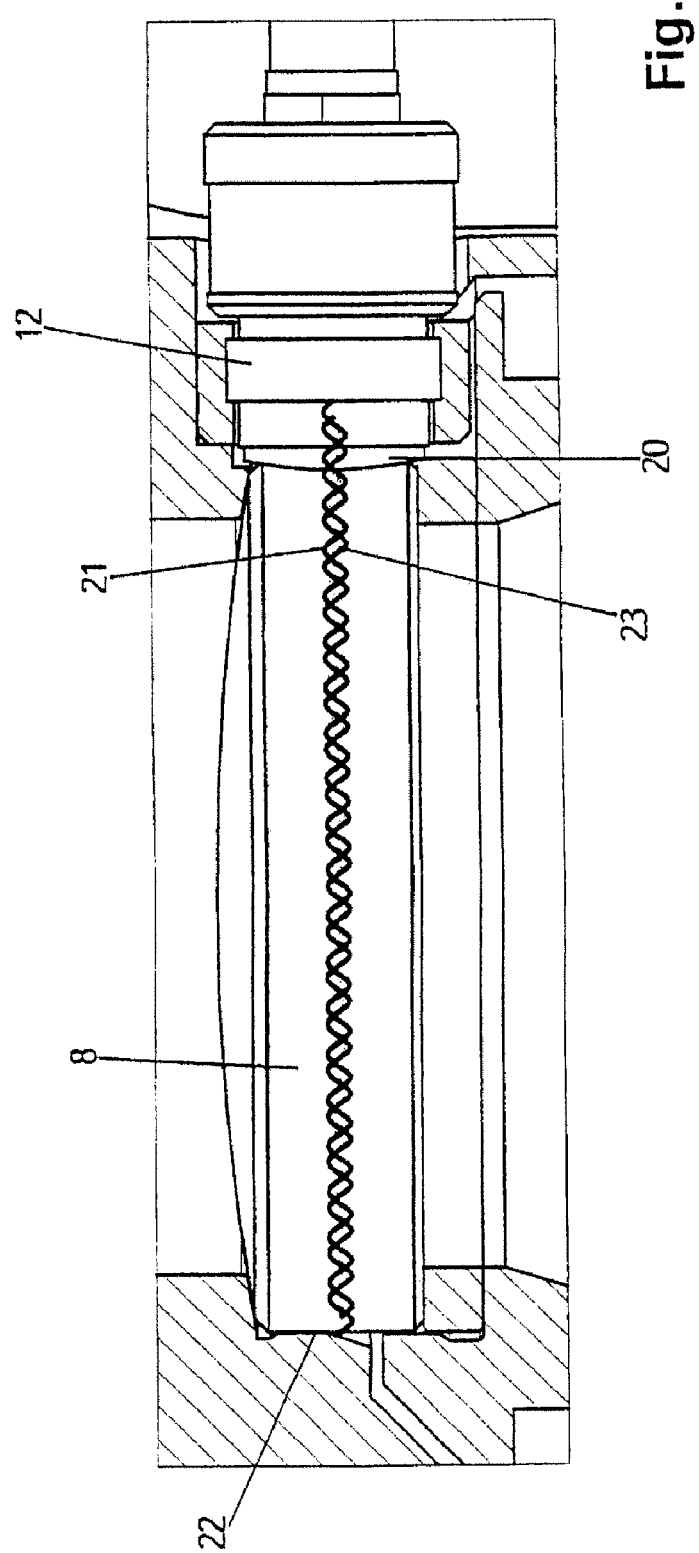
FIG. 2 is an illustration of a partial section of a laser processing head.

Referring to FIG. 2, the detection device 12 is next to a side of an optical element, which, in the example shown in FIG. 2, is the focusing lens 8. The detection device 12 includes an ultrasonic transmitter and an ultrasonic receiver. A coupling element 20 is between the detection device 12 and the focusing lens 8. In order to prevent reflections between the detection device 10 and the focusing lens 8, at least one coupling element 20 can be located between the ultrasonic transmitter or ultrasonic receiver of the detection device 10 and an edge of the focusing lens 8. By using the coupling element 20 between the detection device 12 and the focusing lens 8, the ultrasonic signal 21 emitted from the ultrasonic transmitter included in the detection device 12 is coupled into the focusing lens 8 and decoupled out of the focusing lens 8 after reflection off of the opposite edge 22 of the focusing lens 8. The coupling element 20 can be clamped on to the edge of the focusing lens 8 in such a way that a sonic cone of the ultrasonic signal 21 emitted from the detection device 12 passes through the center of the focusing lens 8, impinges on the opposite edge 22 of the focusing lens 8, and is reflected from the opposite edge of the focusing lens 8 back to the detection device 12.

In order to improve the coupling of the ultrasonic signal 21 into the focusing lens 8, the coupling element 20 can be geometrically matched to the focusing lens 8. For example, the coupling element 20 can be a deformable coupling pad made of a thermally stable plastic, such as polyurethane.

In the example shown in FIG. 2, the coupling element 20 is a coupling pad, and the coupling pad adapts to the contours of both the detection device 12 and the focusing lens 8. A transmitted ultrasonic signal 21 propagates along a diameter of the focusing lens 8 to the opposite edge 22 of the focusing lens 8, and the opposite edge of 22 acts as a reflector of the focussing lens 8. The ultrasonic signal 21 is reflected from the opposite edge 22 of the focusing lens 8 and arrives as an echo signal 23 at the detection device 12. The transit time of the ultrasonic signal 21, 23 is the difference in time between the moment the ultrasonic signal 21 is transmitted from the detection device 12 and the moment the echo signal 23 arrives at the detection device 12. A change in the transit time of the ultrasonic signal 21, 23 is a comparison between the measured transit time and a reference or baseline transit time. The temperature and the degree of absorption of the optical element (the focussing lens 8) can be deduced from one or more of the transit time and the change in transit time.

To determine a condition or a change of condition of an optical element, such as the focusing lens 8, the ultrasonic signal 21 is fed into the focusing lens 8 and the transit time and/or a change in the transit time of the ultrasonic signal 21 along a prespecified or prespecifiable path through the focusing lens 8 is detected. Although the optical element shown in the example of FIG. 2 is the focusing lens 8, in other examples the optical element can be an element such as a mirror, a lens, or a decoupler included in a laser arrangement or included in the laser. The determined transit time, or the change in transit time, can be compared with a reference or baseline value. The reference value can be determined in a reference value measurement or the reference value can be predefined. The measurement of the transit time can be carried out with standard components, and the measurement of the transit time can take place without affecting the laser arrangement. Even small temperature changes can cause a change in the transit time of the ultrasonic signal 21; thus, the temperature of the optical element can be measured or determined with a high resolution. A suitable choice of the path of the ultrasonic signal 21 through the focusing lens 8 can ensure that only the actual temperature, or the associated transit time or transit time change caused by a temperature change in the optical element, is detected, such that the temperature measurement is not distorted by the temperature of, for example, of a holder of the focusing lens 8. In some implementations, the resolution of the transit time measurement is in the nanosecond region.

In one implementation, a degree of absorption of the electromagnetic radiation of the laser beam 5, or a change in the degree of absorption by the focusing lens 8, can be determined from the transit time of the ultrasonic signal 21 and/or the transit time change of the ultrasonic signal 21. Thus, by determining the transit time or a change in the transit time, conclusions can be drawn as to contamination or wear, for example, as a consequence of ageing phenomena, in the focusing lens 8. Additionally, the technique can distinguish between a change in transit time due to a normal temperature change (heating) of the optical element in operation and a change in transit time due to an absorption related temperature increase.

The temperature or a temperature change of the focusing lens 8 can be deduced from the transit time of the ultrasonic signal 21 and/or transit time change of the ultrasonic signal 21. A measure for the wear is provided by both the constant, stable temperature of the optical element and a temporal temperature gradient. Using the transit time measurement, the temperature of the optical element averaged over the path covered by the ultrasonic signal can be determined.

Referring to FIGS. 3A-3D, example paths covered by the ultrasonic signal 21 as the ultrasonic signal 21 traverses the focusing lens 8 are shown. Referring to FIG. 3A, a top view of the focusing lens 8 is shown. In the example shown in FIG. 3A, the ultrasonic signal 21, which is transmitted by the detection device 12, arrives back at the detection device 12 after traversing the focusing lens 8 twice. The path covered by the ultrasonic signal passes through a midpoint 38 of the focussing lens 8. The midpoint 38 is located in the center of the focusing lens 8. Thus, in the example of FIG. 3A, the specified or specifiable path covered by the ultrasonic signal 21 is chosen in such a way that the ultrasonic signal 21 passes through the center of the focusing lens 8. For example, the specified or specifiable path can be chosen to pass through the midpoint 38 of the focusing lens 8. Selecting such a path allows the temperature in the center of the focusing lens 8 to be determined, or at least the temperature in the center is included in the temperature averaged over the path covered by the ultrasonic signal 21. The temperature can thus be detected in the part of the focusing lens 8 that is heated the most when a laser beam traverses the focusing lens 8.

Referring to FIG. 3B, the midpoint 38 of the focusing lens 8 is not included on the path covered by the ultrasonic signal 21. The ultrasonic signal 21 is reflected at the points 25, 26, which are on an edge of the focusing lens 8, before the ultrasonic signal arrives back at the detection device 12. In the example shown in FIG. 3B, the path covered by the ultrasonic signal 21 has a triangular shape, and that the path covered by the ultrasonic signal 21 includes only peripheral regions of the focusing lens 8. Thus, the midpoint 38 of the focussing lens 8 has a negligible influence on the determination of the transit time or of the temperature in the example shown in FIG. 3B.

When the path of the ultrasonic signal 21 includes peripheral regions of the focusing lens 8, information on wear and contamination in the peripheral regions of the optical element can be determined. Peripheral regions of the focusing lens 8 can include regions that do not include the center of the focusing lens 8 or the midpoint 38 of the focusing lens 8. As shown in the example of FIG. 3B, the ultrasonic signal 21 can pass through the focusing lens 8 multiple times by reflection. The use of reflections offers the possibility of using only one transducer (for sending and receiving the ultrasonic signal) because the ultrasonic signal 21 is coupled into the focusing lens 8 at approximately the same location as the ultrasonic signal 21 is detected. Furthermore, the transit time of the ultrasonic signal 21, and, therefore, the resolution of the system, can be increased using single or multiple reflections. Specific regions of the optical element can be examined by the reflection behaviour of the ultrasound at the edge of the optical element for transit time measurement and therefore for temperature measurement. The ultrasonic signal 21 can be passed through the focusing lens 8 in, for example, a star-shaped path (such as the example shown in FIG. 3C), a triangular path (such as the example shown in FIG. 3B), or a rectangular path (such as the example shown in FIG. 3D).

Referring to FIG. 3C, the ultrasonic signal 21 transmitted through the focusing lens 8 is reflected at the points 27, 28, 29, 30, which are on the edge of the focusing lens 8, before it arrives back at the detection device 12. The points 27, 28, 29, 30 act as reflectors for the ultrasonic signal 21, and in the example shown in FIG. 3C, the path covered by the ultrasonic signal 21 essentially has a star shape. Because of the reflection of the ultrasonic signal 21 at the points 27, 28, 29, 30, the path covered by the ultrasonic signal 21 is lengthened.

Referring to FIG. 3D, the ultrasonic signal 21 is transmitted from the ultrasonic transmitter 31 into the focusing lens 8. The ultrasonic signal 21 is reflected at the points 32, 33, which are on the edge of the focussing lens 8, and the ultrasonic signal 21 arrives at the ultrasonic receiver 34. In the example shown in FIG. 3D, the ultrasonic receiver 34 represents the detection device 10.

Figure 4:
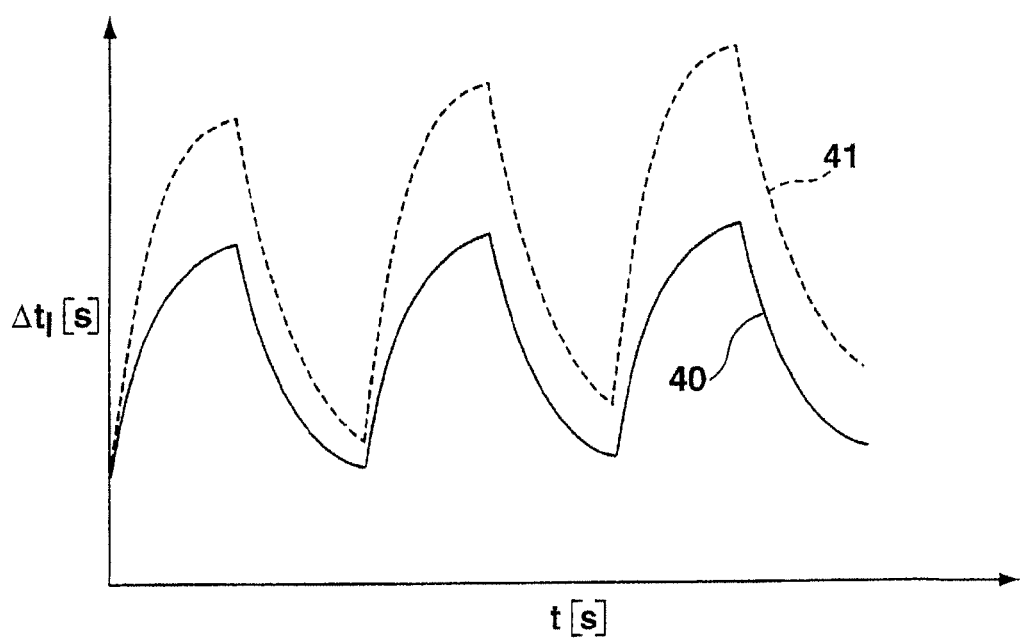
FIG. 4 shows an example of a detected transit time change over time.

Referring to FIG. 4, transit time changes $\Delta t_1$ of the ultrasonic signal are plotted with respect to time. A first curve 40 represents the transit time change $\Delta t_1$ for a new lens with a low degree of absorption. A second curve 41 represents the transit time change $\Delta t_1$ for a slightly contaminated lens with a somewhat higher degree of absorption.

The information shown in FIG. 4 can be collected as the laser is repeatedly switched on and off. During the period when the laser is switched on, the transit time change $\Delta t_1$ increases, because the lens heats up as the lens is irradiated with the laser. From the transit time change $\Delta t_1$ therefore, the temperature of the lens can be deduced. During the switched off period, the lens cools down again, thus the transit time change $\Delta t_1$ falls. It can be seen that the local maxima of the transit time change $\Delta t_1$ increase with increasing time t because the lens does not cool down completely during the period when the laser is switched off. This phenomenon can be taken into account in the analysis of the transit time change $\Delta t_1$. Additionally, the maxima of the transit time change $\Delta t_1$ of the lens with a higher degree (e.g., as represented by the curve 41) of absorption is greater than the maxima of the lens with a lower degree of absorption. This is due to the fact that in the lens with higher absorption, increased laser power is absorbed, which causes the lens to heat up more than the lens with lower absorption. From the comparison of the curves 40, 41 therefore, the temperature of the lenses and the degree of absorption of the lenses can be deduced.

In some implementations, a transit time gradient is determined. The transit time gradient is a change in the transit time over time. From the transit time gradient, a temperature gradient can be determined. When the temperature of an optical element changes, the optical element reacts with a certain delay, which is determined by a time constant associated with the optical element and/or material included in the optical element. The time constant of the optical element can be in the range of, for example, 5-10 seconds. If an absolute temperature is to be detected, the operator waits until the temperature of the optical element is stable. If a temperature gradient is being determined, the measurement can be performed in shorter time intervals. Differences in the absorption of the optical elements can be detected by different gradients of the transit time change. This can supply information on the ageing or the wear of an optical element respectively.

In some implementations, the optical element can be irradiated by electromagnetic radiation, such as laser radiation emitted from a laser, and the transit time and/or transit time change can be detected during the irradiation of the optical element by the electromagnetic radiation and for a specified or specifiable time period after the end of the irradiation. By such a technique, temperature induced transit time changes of an optical element can be determined. During the period when the laser is switched "on," such that the laser emits laser radiation, the optical element warms up. The optical element cools down again after the laser is switched off. If the optical element is irradiated with electromagnetic radiation several times, for example the optical element can be irradiated with electromagnetic radiation over time intervals, perturbations in the measurement of the transit time or the transit time change can be detected. The transit time or transit time change can be detected over prespecified or prespecifiable time intervals. By specifying the time intervals, the resolution of the temperature measurement can be adjusted.

The inspection of the condition of an optical element can take place during operation, such as during a cutting process. This type of inspection can be considered to be quasi "online". Inspection during operation allows rapid reactions to be made to changes in the condition. Alternatively or additionally, at the beginning of a new cutting process, the condition of the optical element can be inspected. For example, if a laser system with low laser power is being used and a temperature change is not detectable at this low laser power, the laser can be operated between two cutting processes at a higher power, so that transit time changes and the condition of the optical element can be determined.

The foregoing description is intended to illustrate and not limit the scope of the techniques discussed above. Other aspects, advantages, and modifications are within the scope of the following claims.

What is claimed is:

1. A method for detecting a condition or detecting a change in the condition of an optical element of a laser arrangement, the method comprising:
    coupling an ultrasonic signal into an optical element such that the ultrasonic signal travels along a path within the optical element; and
    detecting a transit time or a change in transit time for the ultrasonic signal to travel along the path within the optical element.

2. The method of claim 1, wherein detecting a change in transit time comprises detecting a current transit time and comparing the current transit time to a predetermined transit time.

3. The method of claim 1, wherein the path comprises a predetermined path.

4. The method of claim 1, further comprising specifying the path before coupling the ultrasonic signal into the optical element.

5. The method of claim 1, further comprising determining a degree of absorption of electromagnetic radiation of the optical element based on the detected transit time or change in transit time.

6. The method of claim 1, wherein determining a degree of absorption of electromagnetic radiation of the optical element comprises determining a degree of absorption and comparing the degree of absorption to a base degree of absorption.

7. The method of claim 1, further comprising determining a temperature or a change in temperature of the optical element based on the detected transit time.

8. The method of claim 1, wherein the path passes through the center of the optical element.

9. The method of claim 1, wherein the ultrasonic signal is radially coupled into the optical element.

10. The method of claim 1, wherein the path passes through peripheral regions of the optical element without passing through the center of the optical element.

11. The method of claim 1, wherein the path of the ultrasonic signal passes through the optical element multiple times.

12. The method of claim 1, further comprising determining a transit time gradient.

13. The method of claim 1, further comprising:
    irradiating the optical element with electromagnetic radiation, and
    wherein detecting a transit time or a change in transit time of the ultrasonic signal to travel along the path within the optical element comprises detecting the transit time during the irradiation and for a time period following the ending of the irradiation.

14. The method of claim 13, wherein the time period is determined before irradiating the optical element with electromagnetic radiation.

15. The method of claim 13, wherein the electromagnetic radiation comprises laser radiation.

16. The method of claim 13, wherein the optical element is irradiated intermittently with electromagnetic radiation.

17. The method of claim 1, wherein the transit time or transit time change is detected in a set time interval.

18. The method of claim 1, further comprising:
    detecting parameters describing the environment of the optical element; and
    analyzing the transit times based on the detected parameters.

19. The method of claim 18, further comprising:
    generating a characteristic diagram, and
    analyzing a current transit time using the characteristic diagram.

20. A laser arrangement comprising:
    at least one optical element arranged in the beam path of a laser beam;
    a detection device for detecting a parameter of the optical element that varies with a change in temperature;
    an ultrasonic transmitter configured to couple an ultrasonic signal into the optical element; and
    an ultrasonic receiver included in the detection device.

21. The laser arrangement of claim 20, wherein the detection device comprises the ultrasonic transmitter and the ultrasonic receiver.

22. The laser arrangement of claim 20, further comprising at least one reflector configured to reflect the ultrasonic signal.

23. The laser arrangement of claim 20, further comprising:
    at least one coupling element arranged between the optical element and one of the ultrasonic transmitter or the ultrasonic receiver.

24. The laser arrangement of claim 21, wherein the coupling element is matched to the optical element.

25. The laser arrangement of claim 20, further comprising an analysis device connected to the detection device.

26. The laser arrangement of claim 20, wherein the at least one optical element includes one or more of a lens and a mirror.

* * * * *